(12) United States Patent
Fletcher et al.

(10) Patent No.: US 10,132,726 B2
(45) Date of Patent: Nov. 20, 2018

(54) PAPER TRANSIT TICKETS AS A MEDIUM FOR ENVIRONMENTAL SAMPLING

(71) Applicant: Cubic Corporation, San Diego, CA (US)

(72) Inventors: Graham Paul Fletcher, Stanford in the Vale (GB); Steffen Reymann, Reigate (GB); Niosha Kayhani, Sutton (GB)

(73) Assignee: Cubic Corporaton, San Diego, CA (US)

( * ) Notice: Subject to any disclaimer, the term of this patent is extended or adjusted under 35 U.S.C. 154(b) by 0 days.

(21) Appl. No.: 15/616,355

(22) Filed: Jun. 7, 2017

(65) Prior Publication Data

US 2017/0350796 A1 Dec. 7, 2017

Related U.S. Application Data

(60) Provisional application No. 62/346,921, filed on Jun. 7, 2016.

(51) Int. Cl.
*G01N 1/02* (2006.01)
*G01N 1/22* (2006.01)
(Continued)

(52) U.S. Cl.
CPC ............. *G01N 1/2273* (2013.01); *G01N 1/02* (2013.01); *G01N 1/2214* (2013.01); *G01N 1/31* (2013.01); *G01N 33/528* (2013.01); *G01N 35/00029* (2013.01); *G07B 1/02* (2013.01); *G01N 2001/2826* (2013.01); *G01N 2001/2833* (2013.01); *G01N 2035/00108* (2013.01); *G01N 2035/00168* (2013.01);
(Continued)

(58) Field of Classification Search
CPC ................................................ G01N 2001/022
See application file for complete search history.

(56) References Cited

U.S. PATENT DOCUMENTS 9,575,046 B1 2/2017 Laquidara
2003/0085266 A1 5/2003 Simon
2009/0072024 A1* 3/2009 Bonneau, Jr. .......... G06Q 10/06
235/380

FOREIGN PATENT DOCUMENTS

CN 1512165 A 7/2004
WO 03/046515 A1 6/2003
(Continued)

OTHER PUBLICATIONS

International Search Report and Written Opinion dated Sep. 18, 2017 for PCT/US2017/036351; all pages.
(Continued)

*Primary Examiner* — Rosanne Kosson
(74) *Attorney, Agent, or Firm* — Kilpatrick Townsend and Stockton, LLP (57) ABSTRACT

A method for conducting environmental sampling includes determining to environmentally sample a particular paper transit ticket for a specific residue. Using an automated ticket device, at least one chemical reagent is applied to the particular paper transit ticket. The chemical reagent is selected based on the specific residue. The particular paper transit ticket is collected after the particular paper transit ticket was used as a fare media within a transit system. The at least one chemical reagent is analyzed to determine whether any of the specific residue is present.

11 Claims, 6 Drawing Sheets

(51) Int. Cl.
    G01N 1/31      (2006.01)
    G01N 33/52     (2006.01)
    G01N 35/00     (2006.01)
    G07B 1/02      (2006.01)
    G06Q 30/02     (2012.01)
    G07B 15/00     (2011.01)
    G07B 5/00      (2006.01)
    G01N 1/28      (2006.01)

(52) U.S. Cl.
    CPC ........... G06Q 30/0284 (2013.01); G07B 5/00 (2013.01); G07B 15/00 (2013.01)

(56) References Cited

FOREIGN PATENT DOCUMENTS

| | | |
|---|---|---|
| WO | 03046515 A1 | 6/2003 |
| WO | 2006/096246 A1 | 9/2006 |
| WO | 2006-096246 A1 | 9/2006 |
| WO | 2012/054103 A1 | 4/2012 |
| WO | 2012-054103 A1 | 4/2012 |

OTHER PUBLICATIONS

Kathleen Savage, Ph. D, et al., "Firearm Examiner Training," "Modified Griess Test", 1 page, Retrieved from https://projects.nfstc.org/firearms/module12/fir_m12_t05_03_a.htm.
Sirchie, Nark II Methamphetamine/MDMA Reagent, Retrieved from http://www.sirchie.com/nark-ii-sodium-nitro-prusside-reagent-methamphetamine-mdma-10-tests.html#.WxG2FXmWw6Z.
BBI Detection, Narcotics & Cannabis Test Kits, Retrieved from http://www.bbidetection.com/products/narcotics-cannabis-test-kits/.
TechLink, Army Explosive residue detection kit, Retrieved from https://techlinkcenter.org/technologies/explosive-residue-detection-kit/.
Hygiena, PRO-Clean Surface Protein Residue Test, Retrieved from http://jornades.uab.cat/workshopmrama/sites/jornades.uab.cat.workshopmrama/files/PRO_Clean_SpotCheck_Plus_English.pdf.
Scott Company, Cocaine Residue Swab, Retrieved from http://www.scottcompany.com/Info_Page_Coc_Res.html.
MEDIMPEX United Inc., Drugs Residue Identification Tests, Retrieved https://www.meditests.com/drugs-residue-tests.html.
PCT International Search Report and Written Opinion dated Sep. 18, 2017; International Application No. PCT/US2017/036351, all pages.
Firearm Examiner Training, "Modified Griess Test" downloaded from website https://projects.nfstc.org/firearms/module12/fir_m12_t05_03_a.htm, Aug. 13, 2018, 1 page.
Firearm Examiner Training, "Chemistry", 1 of 3, downloaded from website https://projects.nfstc.org/firearms/module12/fir_m12_t05_03_b.htm, Aug. 13, 2018, 1 page.
Firearm Examiner Training, "Reagents and Test Media", 1 of 3, downloaded from website https://projects.nfstc.org/firearms/module12/fir_m12_t05_03_c.htm, Aug. 13, 2018, 1 page.
Firearm Examiner Training, "Test Procedure", 1 of 3, downloaded from website https://projects.nfstc.org/firearms/module12/fir_m12_t05_03_d.htm, Aug. 13, 2018, 1 page.
Firearm Examiner Training, "Reverse Modified Griess Test" downloaded from website https://projects.nfstc.org/firearms/module12/fir_m12_t05_03_e.htm, Aug. 13, 2018, 1 page.
Firearm Examiner Training, "Dithiooxamide Test" downloaded from website https://projects.nfstc.org/firearms/module12/fir_m12_t05_03_f.htm, Aug. 13, 2018, 1 page.
Firearm Examiner Training, "Chemistry", 2 of 3, downloaded from website https://projects.nfstc.org/firearms/module12/fir_m12_t05_03_g.htm, Aug. 13, 2018, 1 page.
Firearm Examiner Training, "Reagents and Test Media", 2 of 3, downloaded from website https://projects.nfstc.org/firearms/module12/fir_m12_t05_03_h.htm, Aug. 13, 2018, 1 page.
Firearm Examiner Training, "Test Procedure", 2 of 3, downloaded from website https://projects.nfstc.org/firearms/module12/fir_m12_t05_03_i.htm, Aug. 13, 2018, 1 page.
Firearm Examiner Training, "Sodium Rhodizonate Test" downloaded from website https://projects.nfstc.org/firearms/module12/fir_m12_t05_03_j.htm, Aug. 13, 2018, 1 page.
Firearm Examiner Training, "Chemistry", 3 of 3, downloaded from website https://projects.nfstc.org/firearms/module12/fir_m12_t05_03_k.htm, Aug. 13, 2018, 1 page.
Firearm Examiner Training, "Reagents and Test Media", 3 of 3, downloaded from website https://projects.nfstc.org/firearms/module12/fir_m12_t05_03_l.htm, Aug. 13, 2018, 1 page.
Firearm Examiner Training, "Test Procedure", 3 of 3, downloaded from website https://projects.nfstc.org/firearms/module12/fir_m12_t05_03_m.htm, Aug. 13, 2018, 1 page.
Firearm Examiner Training, "Bashinski Transfer" downloaded from website https://projects.nfstc.org/firearms/module12/fir_m12_t05_03_n.htm, Aug. 13, 2018, 1 page.
Evident, "Nark II Methamphetamine/MDMA Reagent—10 tests" downloaded from website https://www.shopevident.com/product/nark-ii-methamphetaminemdma-reagent-10-tests, Aug. 13, 2018, 6 pages.
Evident, "Nark II Marquis Opium Alkaloids Reagent—10 tests" downloaded from website https://www.shopevident.com/product/nark-ii-marquis-opium-alkaloids-reagent-10-tests, Aug. 13, 2018, 4 pages.
Evident, "Nark II Nitric Acid Heroin/Morphine Reagent—10 tests" downloaded from website https://www.shopevident.com/product/nark-ii-nitric-acid-heroinmorphine-reagent-10-tests, Aug. 13, 2018, 4 pages.
Evident, "Nark II Dille-Koppanyi Barbiturates Reagent—10 tests" downloaded from website https://www.shopevident.com/product/nark-ii-dille-koppanyi-barbiturates-reagent-10-tests, Aug. 13, 2018, 8 pages.
Evident, "Nark II Ehrlich's (Modified) LSD Reagent—10 tests" downloaded from website https://www.shopevident.com/product/nark-ii-ehrlichs-modified-lsd-reagent-10-tests, Aug. 13, 2018, 12 pages.
Evident, "Nark II Duquenois-Levine Marijuana Reagent—10 tests" downloaded from website https://www.shopevident.com/product/nark-ii-duquenois-levine-marijuana-reagent-10-tests, Aug. 13, 2018, 12 pages.
Evident, "Nark II Acid Neutralizer—1 oz. bottle" downloaded from website https://www.shopevident.com/product/nark-ii-acid-neutralizer-1-oz-bottle, Aug. 13, 2018, 4 pages.
Evident, "Nark II Scott Cocaine Salts Reagent (modified)—10 tests" downloaded from website https://www.shopevident.com/product/nark-ii-scott-cocaine-salts-reagent-modified-10-tests, Aug. 13, 2018, 12 pages.
Evident, "Nark II Methadone Reagent—10 tests" downloaded from website https://www.shopevident.com/product/nark-ii-methadone-reagent-10-tests, Aug. 13, 2018, 7 pages.
Evident, "Nark II PCP/ Methaqualone Reagent—10 tests" downloaded from website https://www.shopevident.com/product/nark-ii-pcp-methaqualone-reagent-10-tests, Aug. 13, 2018, 9 pages.
Evident, "Nark II Special Opiates Heroin/Oxycodone Reagent—10 tests" downloaded from website https://www.shopevident.com/product/nark-ii-special-opiates-heroinoxycodone-reagent-10-tests, Aug. 13, 2018, 4 pages.
Evident, "Nark II Mecke's All Heroin (Modified) Reagent—10 tests" downloaded from website https://www.shopevident.com/product/nark-ii-meckes-all-heroin-modified-reagent-10-tests, Aug. 13, 2018, 8 pages.
Evident, "Nark II Talwin (Pentazocine) Reagent—10 tests" downloaded from website https://www.shopevident.com/product/nark-ii-talwin-pentazocine-reagent-10-tests, Aug. 13, 2018, 8 pages.
Evident, "Nark II Ephedrine/Pseudoephedrine Reagent—10 tests" downloaded from website https://www.shopevident.com/product/nark-ii-ephedrinepseudoephedrine-reagent-10-tests, Aug. 13, 2018, 8 pages.

(56) References Cited

OTHER PUBLICATIONS

Evident, "Nark II Valium/Rohypnol/Ketamine Reagent—10 tests" downloaded from website https://www.shopevident.com/product/nark-ii-valiumrohypnolketamine-reagent-10-tests, Aug. 13, 2018, 8 pages.

Evident, "Nark II Methamphetamine/MDMA Reagent—10 tests" downloaded from website https://www.shopevident.com/product/nark-ii-methamphetaminemdma-reagent-10-tests, Aug. 13, 2018, 12 pages.

Evident, "Nark II Progressive Identification Card" downloaded from website https://www.shopevident.com/product/nark-ii-progressive-identification-card, Aug. 13, 2018, 1 page.

Evident, "Nark II Progressive Identification Wall Chart" downloaded from website https://www.shopevident.com/product/nark-ii-progressive-identification-wall-chart, Aug. 13, 2018, 1 page.

Evident, "Nark II Drug Field Test Results Log—25 sheets" downloaded from website https://www.shopevident.com/product/nark-ii-drug-field-test-results-log-25-sheets, Aug. 13, 2018, 1 page.

Evident, "Nark II Mayer's Narcotic Alkaloids Reagent—10 tests" downloaded from website https://www.shopevident.com/product/nark-ii-mayers-narcotic-alkaloids-reagent-10-tests, Aug. 13, 2018, 4 pages.

Evident, "Nark II KN Marijuana (green plants/seeds) Reagent—10 tests" downloaded from website https://www.shopevident.com/product/nark-ii-kn-marijuana-green-plantsseeds-reagent-10-tests, Aug. 13, 2018, 9 pages.

Evident, "Nark II GHB Reagent—5 tests" downloaded from website https://www.shopevident.com/product/nark-ii-ghb-reagent-5-tests, Aug. 13, 2018, 4 pages.

Evident, "Nark II Mandelin Methadone Reagent—10 tests" downloaded from website https://www.shopevident.com/product/nark-ii-mandelin-methadone-reagent-10-tests, Aug. 13, 2018, 1 page.

Evident, "Nark II Synthetic Marijuana (K2, Spice) Reagent—5 tests" downloaded from website https://www.shopevident.com/product/nark-ii-synthetic-marijuana-k2-spice-reagent-5-tests, Aug. 13, 2018, 1 page.

Evident, "Nark II MDPV Bath Salts Reagent—10 tests" downloaded from website https://www.shopevident.com/product/nark-ii-mdpv-bath-salts-reagent-10-tests, Aug. 13, 2018, 2 pages.

Evident, "Nark II Mephedrone Bath Salts Reagent—10 tests" downloaded from website https://www.shopevident.com/product/nark-ii-mephedrone-bath-salts-reagent-10-tests, Aug. 13, 2018, 2 pages.

Evident, "Nark II a-PVP Bath Salts Reagent—10 tests" downloaded from website https://www.shopevident.com/product/nark-ii-pvp-bath-salts-reagent-10-tests, Aug. 13, 2018, 2 pages.

Evident, "Nark II 2C Synthetic Cathinones Reagent—10 tests" downloaded from website https://www.shopevident.com/product/nark-ii-2c-synthetic-cathinones-reagent-10-tests, Aug. 13, 2018, 2 pages.

Evident, "Nark II Psilocybin Mushrooms Reagent—10 tests" downloaded from website https://www.shopevident.com/product/nark-ii-psilocybin-mushrooms-reagent-10-tests, Aug. 13, 2018, 2 pages.

Evident, "Nark II Liebermann Meth/Morphine Reagent—tests" downloaded from website https://www.shopevident.com/product/nark-ii-liebermann-methmorphine-reagent-10-tests, Aug. 13, 2018, 2 pages.

Evident, "Nark II Molly/Ecstasy/MDMA Reagent—10 tests" downloaded from website https://www.shopevident.com/product/nark-ii-mollyecstasymdma-reagent-10-tests, Aug. 13, 2018, 2 pages.

Evident, "Nark II Fentanyl Reagent—10 tests" downloaded from website https://www.shopevident.com/product/nark-ii-fentanyl-reagent-10-tests, Aug. 13, 2018, 2 pages.

* cited by examiner

PAPER TRANSIT TICKETS AS A MEDIUM FOR ENVIRONMENTAL SAMPLING

CROSS-REFERENCES TO RELATED APPLICATIONS

This application claims priority to U.S. Provisional Patent Application No. 62/346,921, filed Jun. 7, 2016, entitled "PAPER TRANSIT TICKETS AS A MEDIUM FOR ENVIRONMENTAL SAMPLING," the entire disclosure of which is hereby incorporated by reference, for all purposes, as if fully set forth herein.

BACKGROUND OF THE INVENTION

Current forms of biological testing typically require the use of complex electronic sensors. These sensors may be costly and may prohibit the geographical coverage of the sampling, as only areas having sensors may be sampled. Environmental testing of currency, such as paper currency, may be possible. However, due to the widespread and longstanding circulation of currency, it is very difficult to determine when or where any particular contaminant was detected. Moreover, some reagents are not particularly safe for human contact, so the application of such reagents may require pulling the currency out of circulation. Cheaper and more robust environmental sampling techniques are desired.

BRIEF SUMMARY OF THE INVENTION

Embodiments of the present invention are generally related to widespread sampling of a city environment for chemical and/or biological residue. It will be understood, however, that locations and/or application for the present invention are not so limited. Embodiments of the present invention provide sampling techniques that apply one or more chemical reagents to paper transit tickets to detect the presence of one or more contaminants. Because of the nature of transit tickets, at least a portion of transit tickets may follow a generally known path (i.e. a transit route) over a kwon period of time (based on a period of validity of the tickets). Using such information, data regarding the presence of particular contaminants in a specified location and/or at a specific time may be determined.

In one aspect, a method for conducting environmental sampling is provided. The method may include determining to environmentally sample a particular paper transit ticket for a specific residue and applying, using an automated ticket device, at least one chemical reagent to the particular paper transit ticket. The chemical reagent may be selected based on the specific residue. The method may also include collecting the particular paper transit ticket after the particular paper transit ticket was used as a fare media within a transit system and analyzing the at least one chemical reagent to determine whether any of the specific residue is present.

In another aspect, a method for conducting environmental sampling includes receiving, at an automated ticket device, a number of paper transit tickets and scanning, using the automated ticket device, data from each of the paper transit tickets. The method may also include sorting the paper transit tickets according to the data read from each of the paper transit tickets. The sorting may be based on which of the plurality of paper transit tickets are to be environmentally sampled. A subset of the sorted paper transit tickets may include tickets that are to be environmentally tested for a particular contaminant.

In another aspect, an automated ticket device for use in environmental sampling is provided. The ticket device may include a ticket receiving mechanism configured to receive a plurality of paper transit tickets and a ticket scanner configured to read data on each of the plurality of paper transit tickets. The ticket device may also include a sorting mechanism configured to sort the plurality of paper transit tickets according to the data read from each of the plurality of paper transit tickets. The sorting may be based on which of the plurality of paper transit tickets are to be environmentally sampled. A subset of the sorted plurality of paper transit tickets may be tickets that are to be environmentally tested for a particular contaminant.

DETAILED DESCRIPTION OF THE INVENTION

Printing of chemical reagents onto paper is a relatively new technology. Printing the necessary chemicals and processes onto paper to perform testing for chemical and/or biological residue such as various types of air pollution, anthrax spores, and/or explosive residue is possible. Without such reagents, complex electrical sensors have to be used to detect many sorts of pollutants or other contaminants. According to embodiments of the invention, such reagents may be placed on and/or in a paper transit ticket, which makes it possible to sample an area of a city or other municipality in which the transit system is located while maintaining the anonymity of the people carrying the tickets.

Paper transit tickets are unique media for environmental sampling, as they are the only (or one of a few) paper elements that do not circulate like cash, but yet are still carried in people's hands, wallets, bags, and/or other carriers where the tickets are exposed to the environment and are used on a defined route or within a defined area, oftentimes during a defined time period. This makes transit tickets ideal for controlled studies of pollutants and/or other contaminants.

Embodiments of the environmental sampling techniques described herein provide numerous advantages. For example, tickets may be carried in pockets, bags, wallets, and/or by hand. In all these places the tickets are exposed to the environment and/or are alongside other objects that are exposed to the environment. Thus, the tickets themselves become exposed to a number of contaminants. Moreover, paper (on which the tickets are printed) is an excellent absorbent of many pollutants. Tickets may travel over a very well defined route, such as a transit route associated with a particular transit ticket, and within a well understood timeframe, making the tickets unique among paper goods. Tickets bought for transit purposes can be tested anonymously, thus making the tickets an ideal medium for sampling the population without breaching confidentiality. In some embodiments, chemical reagents may be printed using modified ink jet printers, making the technology very inexpensive to deploy.

In addition to transit applications, embodiments of the environmental sampling techniques described herein may be utilized in any application that uses paper tickets. The tickets may be used to sample for pollution, genetic markers, infectious diseases, and/or indicators of general health and well-being.

Figure 1:
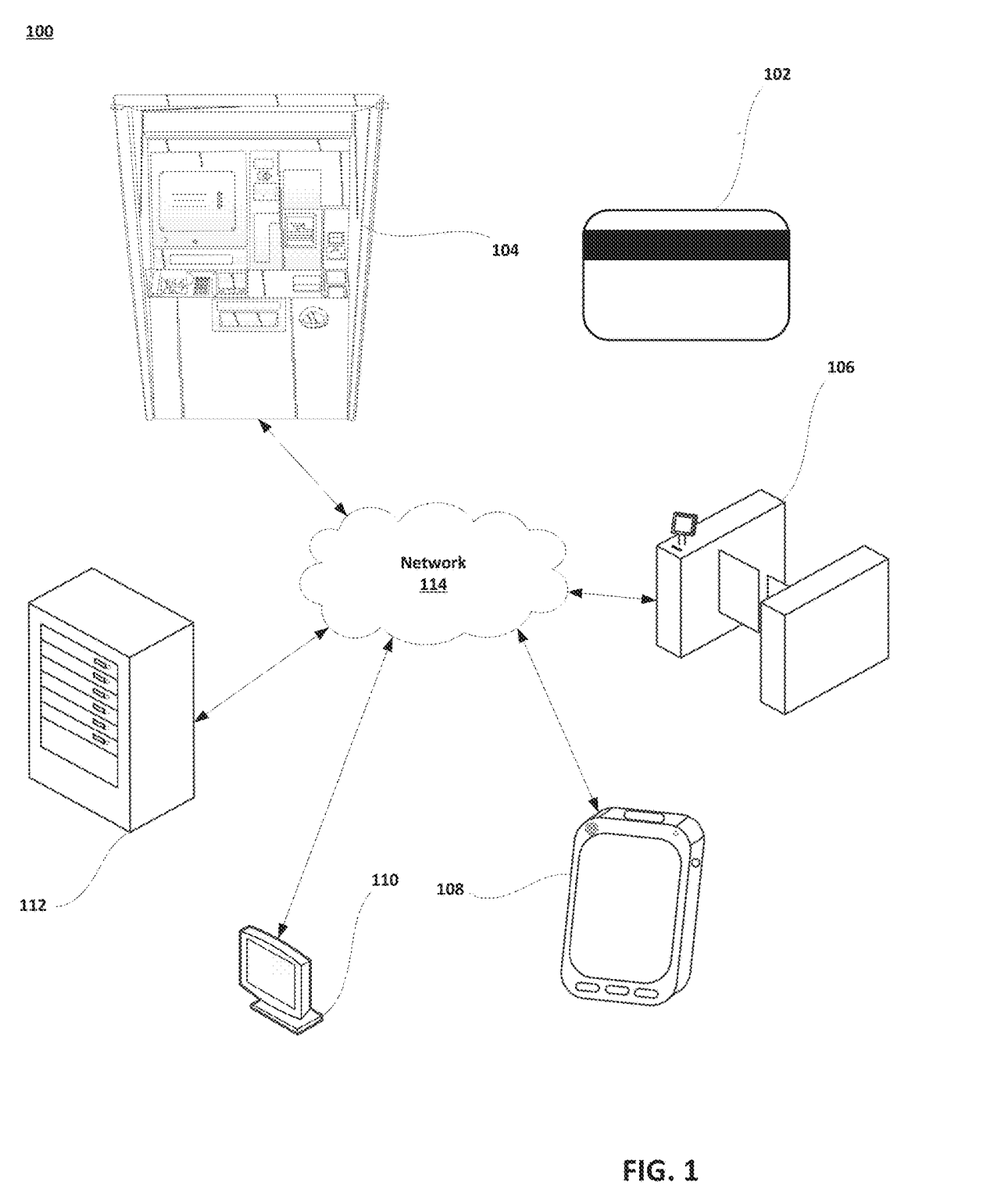
FIG. 1 depicts a system for conducting environmental sampling using paper transit tickets according to embodiments.

Turning now to FIG. 1, a system 100 for conducting environmental sampling is shown. System 100 may include a plurality of paper transit tickets 102. The paper transit tickets 102 may be issued by a transit system for use as access media within the transit system. As the paper tickets 102 are exposed to the environment, the paper comes into contact with and/or absorbs residue from any number of contaminants, such as pollutants, drug residue, and the like. These contaminants may be detected using one or more chemical reagents that may be applied to the tickets 102.

The tickets 102 may be generated and/or collected using one or more automated ticket devices such as vending machines, ticket validators at transit stops and/or on transit vehicles, door entry devices, parking and/or transit entry and/or exit controllers, portable hand-held ticket validation devices and/or any other ticket readers, issuers and/or collectors. For example, one or more transit ticket vending machines 104 may be configured to print and/or otherwise generate the transit tickets 102. Additionally, one or more ticket collection devices 106 and/or portable fare devices 108 may be used to collect and/or sort used tickets for environmental sampling. In some embodiments, one or more of the automated ticket devices may be configured to apply chemical reagents to the paper transit tickets. For example, a ticket vending machine 104 may be configured to print or otherwise apply one or more chemical reagents to some or all of the paper transit tickets 102 prior to issuing the transit tickets 102. When a customer purchases a transit ticket 102 matching criteria for environmental testing (such as a ticket 102 useable for a particular transit route, valid during a particular timeframe, a ticket 102 being issued to a customer matching particular demographic information, other criteria, and/or combinations thereof) the vending machine 104 may determine that one or more chemical reagents must be applied to the ticket 102 at the time of issuance. The vending machine 104 may then print or otherwise apply one or more of the chemical reagents to the ticket 102. In some embodiments, once used and collected, these transit tickets 102 may be sorted into one or more stacks of tickets 102 for analysis of the reagent(s). Oftentimes, this involves a ticket collection devices 106 and/or portable fare devices 108 collecting and/or sorting the tickets 102 based on which tickets 102 are to be environmentally sampled, such as by using ticket fare information present on each of the transit tickets 102. Subsets of tickets with matching reagent(s) (or lack thereof) may be separated and stored in separate stacks or compartments within the ticket collection devices 106 and/or portable fare devices 108, thus ensuring that the reagents do not pick up contaminants and/or reagents from tickets in different subsets.

In other embodiments, such as those where the chemical reagents are to be applied after the paper ticket 102 has been redeemed or otherwise used for access to the transit system, automated ticket devices such as ticket collection devices 106 and/or portable fare devices 108 may collect used tickets 102. The used tickets 102 may be sorted into various subsets. Oftentimes this may be done automatically using the ticket collection devices 106 and/or portable fare devices 108. The sorting may be done based on ticket information stored on the paper tickets 102. As just one example, the paper transit tickets may include printed and/or magnetically encoded information regarding what transit fare type each of the paper tickets 102 represents. The ticket collection devices 106 and/or portable fare devices 108 may then read the data from the tickets 102, such as by using optical imagers and/or magnetic data readers. The information read from the tickets 102 may be compared with a list of ticket types that have been selected for environmental sampling. In some embodiments, the list of ticket types and/or other criteria used to select tickets for environmental sampling may be provided by a back office 112 and/or a remote source. As just one example, a municipality may determine which contaminants and/or locations are to be tested. This information may be communicated to the back office 112, which may determine which type of tickets (fare type, transit system region, and/or other criteria) most closely match the contaminants and/or locations provided by the municipality or other source. The back office 112 may then create one or more lists of ticket types to be retained and/or otherwise collected for environmental sampling. Those tickets 102 matching the ticket types for environmental sampling may be sorted into one or more different subsets, with those tickets not being environmental sampling being sorted into their own subset and/or discarded entirely. In some embodiments, upon collecting the ticket 102 and identifying the ticket 102 for environmental sampling, the ticket collection devices 106 and/or portable fare devices 108 may automatically print and/or otherwise apply one or more reagents to the collected ticket 102. In other embodiments, the sorted tickets may be sent in bulk to a lab 110 and/or other location for application of the chemical reagent(s).

The chemical reagents may be used to detect the presence of particular contaminants and/or the presence of disease markers. As just one example, 2,2'-azino-bis(3-ethylbenzo-thiazoline-6-sulphonic acid) (ABTS), glucose oxidase (GOx), and/or horse-radish peroxidase (HRP) may be printed onto a ticket to measure markers of diabetes. In some embodiments, multiple reagents may be applied to a single ticket to detect the present of multiple contaminants. The type of reagent being applied may determine where and when the reagent is applied to the paper transit tickets 102. For example, some reagents may be hazardous to humans and/or have short reactive lifespans. Such reagents may necessitate that the reagents are applied after the paper transit tickets 102 have been used and collected to minimize and/or prevent human contact with the reagents. For reagents that are safe and/or have a longer reactive lifespan, the reagent may be applied prior to the ticket 102 being issued to a transit customer. Using such characteristics of a chemical reagent, it may be determined what, if any, automated ticket device is used to apply the reagent. In some embodiments, one or more reagents may be applied to the tickets 102 after the tickets 102 are collected by an automated ticket device. For example, the collected tickets 102 may be sent to a remote location, such as a lab 110, for application of the chemical reagent(s). In some embodiments, a particular paper transit ticket 102 may include both reagents applied before and after issuance of the transit ticket 102.

Selection of which reagents are to be applied to transit tickets 102 may be based on other factors, alone or in addition to characteristics of the particular reagents. For example, the reagents may be selected based on a type of contaminant being detected in a particular area. The particular area may represent an entire municipality and/or metropolitan area and/or may represent only a section of a municipality and/or metropolitan area. In some embodiments, the particular area may coincide with one or more transit routes. In such embodiments, transit tickets 102 matching the transit routes coinciding with a particular area may be treated with reagents to test for specific contaminants. This allows only relevant tickets 102 to include the reagents, while allowing tickets 102 representing different areas to be treated with different reagents or combinations thereof and/or no reagents at all.

Oftentimes, the analysis of the various chemical reagents may be conducted using a separate lab 110. For example, once the tickets 102 are collected and/or sorted, the transit system may send the collected tickets 102 to the lab 110 for subsequent analysis and/or application of chemical reagents. The lab 110 may determine whether tickets 102 contain any contaminants by analyzing any reactions found using the chemical reagent(s) on each ticket 102. Each subset of tickets (based on ticket information such as fare type, time of day, other route information, etc.) may be analyzed to get a picture of the contamination of a particular contaminant within a city or partial area thereof. The analysis may not only show whether a particular contaminant is present, but may also determine a concentration level, such as using parts per million (ppm) or other measurements. The results of this analysis may be compared to historical information to determine a trend of the specific residue in a particular location. For example, sampling data from a particular transit route and/or location within a city may be monitored to determine whether the presence of a particular contaminant has increased or decreased. Such information may be transmitted to the back office 112 and/or other remote source, such as a municipal entity. This allows for the data to be usable in transit/city planning efforts.

While described here with the analysis being done at a remote lab 110, it will be appreciated that in some embodiments, analytic equipment, such as scanning mechanisms that can detect the presence of (and possibly quantity of) a particular contaminant that comes into contact with a particular reagent, may be provided on the ticket collection devices described herein. This allows for a real-time analysis of the transit tickets 102 that may be used to give a more accurate picture of the contamination of a particular area at a specific time.

Figure 2:
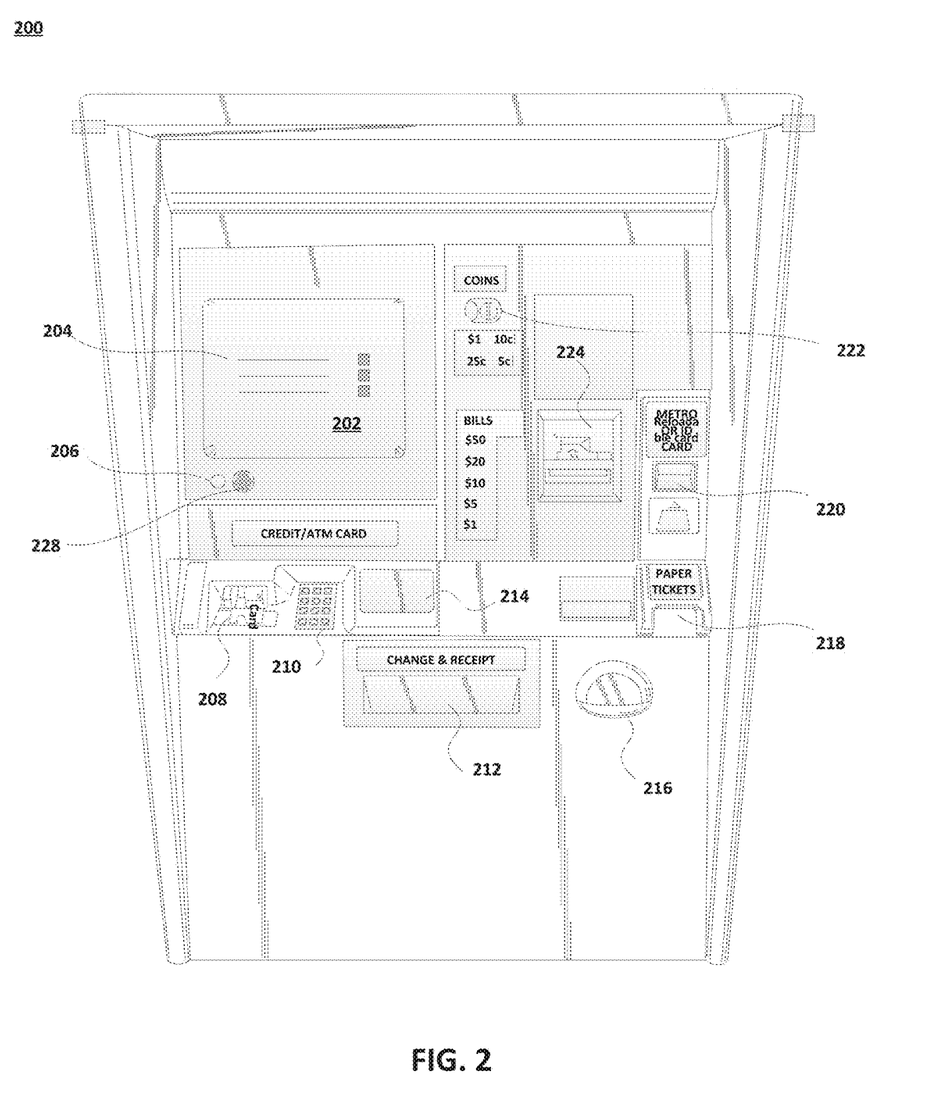
FIG. 2 depicts a vending machine configured for use in an environmental sampling application according to embodiments.

Each of the devices in system 100 may be communicatively coupled using one or more local area networks (LAN) 206 and/or other wired and/or wireless networks 114. Network 114 may utilize one or more of Wi-Fi, ZigBee, Bluetooth™, Bluetooth™ Low Energy, a cellular communications protocol such as 3G, 4G, or LTE, and/or any other wireless communications protocol. It will be appreciated that one or more different network connections may be used in accordance with the invention, and that the use of a single network 114 to enable communications is merely one example of such configurations. For example, each component may be communicatively coupled with other components using a separate network for one or more of the connections. The connections between the vending machine 104, ticket collection device 106, portable fare device 108, lab 110, and/or back office 112 may be secure. This may be done using encryption over a public network, a private network, a secure virtual private network (VPN), or any other method of securing a connection FIG. 2 depicts one embodiment of a ticket vending machine 200. Ticket vending machine 200 may be one of the ticket vending machines 104 described in relation to FIG. 1. In some embodiments. Vending machine 200 may include one or more displays 202 on which information related to products and/or services available from a selected remote source, details related to the transaction, instructions on conducting transactions, videos, and/or any other information may be provided. In some embodiments, vending machine 200 may have a first screen configured to display a user interface to conduct transactions, while a second screen is used to provide instructions and/or host videos, such as video communications with an agent of a ticket office of a transit system. In other embodiments, a single display 202 may be used for displaying all available content. Vending machine 200 may also include one or more input interfaces. For example, input interfaces may include a keypad 210, a touchscreen 204 on display 202, a voice command device such as a microphone 228, and/or any other mechanisms for allowing a user to input information. One or more payment readers may be included on vending machine 200. For example, payment readers may include a cash reader 224, a coin reader 222, a credit and/or debit card reader 208, near field communication (NFC) reader 214. It will be appreciated that other payment readers may be included. In some embodiments, NFC reader 214 is configured to read various types of media, such as smart cards, mobile devices, and other media.

Vending machine 200 may include one or more printers and/or data writers for printing transaction items such as entry tickets, boarding passes, confirmation tickets, vouchers, receipts, and/or any other documentation related to a transaction. For example, a receipt printer 212 may be used to issue receipts of payments, refunds, and/or other transactions. A fare media printer or writer 218 may be included to issue fare media, such as single ride tickets, smart cards, monthly passes, and the like. In some embodiments, change may be returned to a user in coin tray 216 and/or a cash dispenser. In some embodiments, cash dispenser may be a separate component, while in other embodiments, cash returns may be dispensed near receipt printer 212. In some embodiments, transaction items, such as transit media and receipts, will be issued electronically, rather than a printed hard copy being provided. Vending machine 200 may also include a camera, a speaker 206, and/or other audio/visual components to enable audio and/or video communication with a ticket office. Each of the components of the vending machine 200 may be controlled by the vending machine 200 locally, or remotely by a ticket office. For example, vending machine 200 may be operated in a passenger mode where a user may approach the vending machine 200 and interact with the validation device in person and/or in a remote expert mode where an agent from a ticket office controls the software and/or hardware peripherals of the machine, such as when a user needs help completing a transaction.

In some embodiments, the fare media printer 218 may be configured to not only write optical and/or magnetic data to paper transit tickets, but may also be configured to print and/or otherwise apply one or more chemical reagents to the tickets. For example, one or more ink cartridges that contain chemical reagents may be provided in the vending machine 200. This enables the fare media printer 218 to apply the reagent(s) to select tickets. In some embodiments, the application of the one or more chemical reagents may be done using a separate printer of the vending machine 200.

The determination of whether to print or otherwise apply a chemical reagent to a given ticket may be made based on a number of criteria, such as what type of transit fare the ticket is for and/or what region of a city or other area the ticket is likely to circulate in (which may be based on a particular transit route the ticket is designated for use with), and/or other criteria. These criteria may be set by a back office or other remote source that may communicate the criteria to the vending machine 200 using a communications interface. The criteria may include information, such as fare information, related to tickets that are to be environmentally sampled. The criteria may also include one or more types of chemical reagents to be applied to tickets matching a particular set of fare information. These criteria may be stored on a memory of the vending machine 200.

When a ticket is purchased, a processor of the vending machine 200 may compare the ticket information of the selected ticket to the criteria stored in the memory. When the selected ticket information matches the stored criteria, the vending machine 200 may determine that one or more chemical reagents should be applied to a particular ticket, and printer 218 may be used to apply such a reagent to the ticket. Oftentimes, printer 218 will only be used to print reagents onto tickets when the particular reagent is both deemed to be safe for human contact and has a long reactive lifespan. In such a manner, printer 218 may be used to issue paper transit tickets that include one or more chemical reagents at the time of issuance. If the ticket information does not match the stored criteria, the printer 218 may issue a standard paper transit ticket without any chemical reagents. In some embodiments, the criteria supplied to the vending machine 200 may only include criteria for those tickets to include one or more chemical reagents at the time of issuance, while in other embodiments, the criteria may include ticket information for all tickets being environmentally sampled. In such embodiments, the vending machine 200 may make a determination whether a particular reagent is to be applied at the time of issuance, such as by identifying the type of chemical reagent(s) associated with a particular ticket. If the chemical reagent is present in the vending machine 200, the vending machine 200 may determine to apply the reagent to the paper transit ticket prior to issuance.

Figure 3:
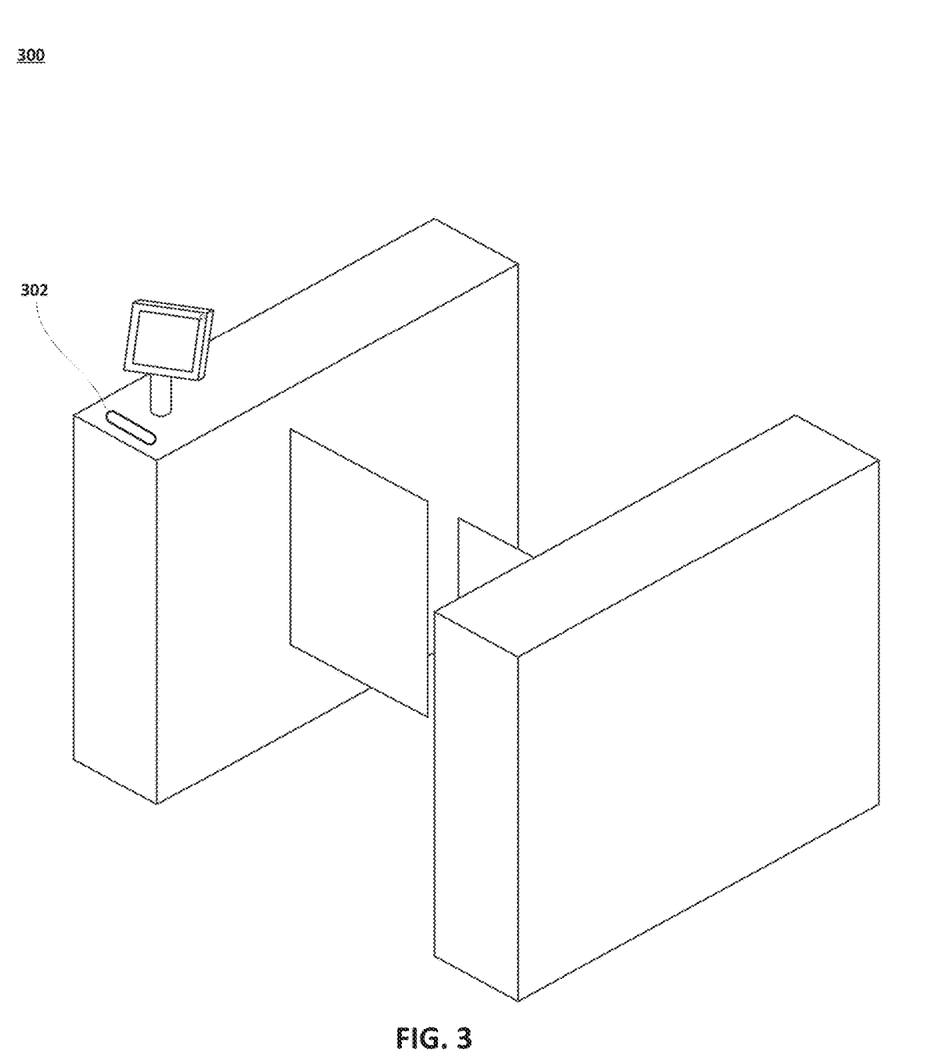
FIG. 3 depicts a ticket collection device configured for use in an environmental sampling application according to embodiments.

FIG. 3 depicts one embodiment of a ticket collection device 300. Ticket collection device 300 may be usable as ticket collection devices 106 in relation to the system 100 described above. Ticket collection device 300 may be used to collect and/or sort used paper transit tickets for environmental sampling purposes. Oftentimes, the ticket collection device 300 may be placed at an entrance or exit at a transit station or other transit stop, serving to collect used transit tickets as customers use the tickets to enter and/or exit the transit system. In some embodiments, the ticket collection device 300 may take the form of a fare gate. The fare gate may be placed at the entrance and/or the exit of a transit station and may require each customer to insert a paper ticket into a ticket feeder 302 in order to gain passage through the ticket collection device 300. For example, upon receiving a proper transit ticket, the ticket collection device 300 read information on the ticket (such as optical and/or magnetic data) to determine whether to grant passage to the user as is known in the art. If passage is to be allowed, the ticket collection device 300 may change a physical state of an access mechanism. For example, a gate or barrier may be moved to allow the user physical access to or from the transit system. In other embodiments, a gate or turnstile may be unlocked to allow a user to pass through the mechanism. In yet other embodiments, a light, sound, and/or other audio and/or visual indication may be emitted from the ticket collection device 300 to indicate that the user is allowed passage.

Along with being used to determine whether to grant passage at the ticket collection device 300, the ticket information may be used by the ticket collection device 300 to sort the collected tickets. For example, the ticket collection device 300 may include a communications interface that is coupled with a back office and/or other remote source that provides criteria for tickets that are to be environmentally sampled. The criteria may not only include data regarding which fare types, dates, times, and/or other ticket information are to be sampled, but may include information related to which chemical reagents are to be used with various subsets of ticket types. These criteria may be stored on a memory of the ticket collection device 300. As tickets are collected and the information is read, the information is compared to the criteria to determine whether each ticket is to be saved for environmental sampling. If the ticket does not match any environmental sampling criteria, the ticket may be sorted by the ticket collection device 300 into a stack, bin, or other receptacle for disposal, such as recycling or waste. If the ticket does match environmental sampling criteria, the ticket may be sorted into a subset of tickets within a stack, bin, or other receptacle of tickets with matching criteria. The ticket collection device 300 may have any number of receptacles in which the various subsets of tickets for environmental sampling may be stored. Oftentimes, each subset of ticket will have its own receptacle to prevent cross-contamination that may skew the results of the sampling.

In some embodiments, once the tickets are sorted into their respective receptacles, the tickets and/or receptacles may be sent to a lab for application of one or more chemical reagents and/or analysis of the chemical reagents (including any applied at issuance, such as by vending machine 200). In other embodiments, the ticket collection device 300 may include a printer (not shown) or other device that is configure to apply one or more chemical reagents to the paper tickets based on the matching criteria as the tickets are sorted. For example, if the ticket collection device 300 receives a ticket that is to be sampled using a particular reagent, the printer may apply the reagent to the ticket prior to placing the ticket in the relevant receptacle. Upon the ticket collection device 300 sorting and applying reagents to the tickets, each receptacle and/or subset of tickets may be sent to a lab for analysis of the tickets.

In some embodiments, the ticket collection device 300 is not a fare gate, and may only serve as a ticket receptacle. However, the ticket receptacle may still be configured to sort and/or apply one or more chemical reagents to selected tickets. In other words, the ticket receptacle may be a computerized smart receptacle with a ticket feeder, data reader, sorting mechanism, and/or reagent application device that may perform each of the functions associated with the ticket collection device 300 in the form of a fare gate, with the exception that the smart receptacle does not control passage of the user into or out of the transit system.

Figure 4:
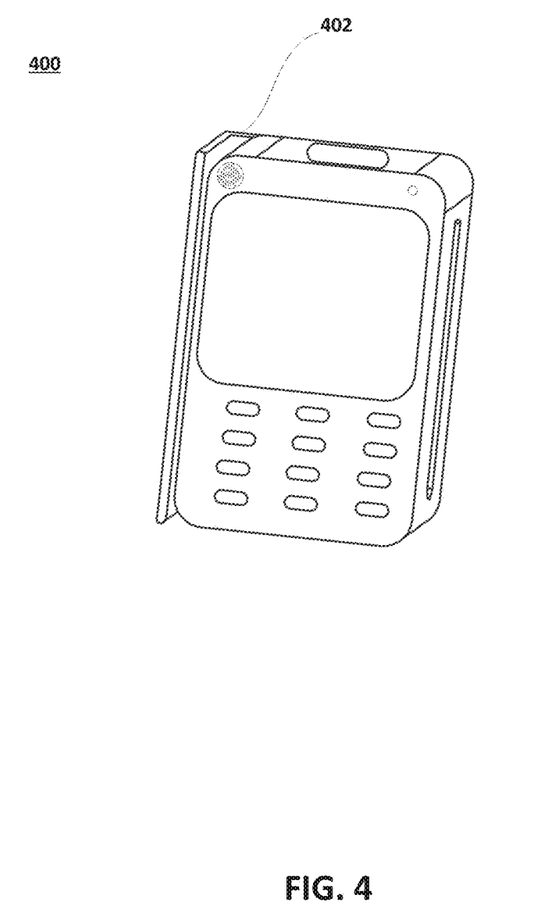
FIG. 4 depicts a portable fare device configured for use in an environmental sampling application according to embodiments.

FIG. 4 depicts one embodiment of a portable fare device 400. Portable fare device 400 may be used as portable fare devices 108 in system 100. Portable fare device 400 may be a mobile device that is carried by transit personnel, such as fare inspectors, and may be used to scan and/or collect paper transit tickets. For example, a fare inspector may be present on a transit vehicle and may scan riders' transit tickets to ensure that all riders have valid transit fare. The portable fare device 400 may include one or more media readers 402, such as an optical and/or magnetic reader that is configured to read transit information from each paper ticket. In some embodiments, an optical reader may require that the ticket be inserted into a feeder of the portable fare device 400 such that the ticket is scanned internally of the portable fare device 400.

The portable fare device 400 may include a communications interface that is coupled with a back office and/or other remote source that provides criteria for tickets that are to be environmentally sampled. The criteria may not only include data regarding which fare types, dates, times, and/or other ticket information are to be sampled, but may include information related to which chemical reagents are to be used with various subsets of ticket types. These criteria may be stored on a memory of the portable fare device 400. As tickets are scanned using the portable fare device 400, the information is compared to the criteria to determine whether each ticket is to be saved for environmental sampling. If the ticket does not match any environmental sampling criteria, the ticket may be returned to the rider or sorted by the portable fare device 400 into a stack, bin, or other receptacle for disposal, such as recycling or waste. If the ticket does match environmental sampling criteria, the ticket may be retained and sorted into a subset of tickets within a stack, bin, or other receptacle of tickets with matching criteria. The portable fare device 400 may have any number of receptacles in which the various subsets of tickets for environmental sampling may be stored. Oftentimes, each subset of ticket will have its own receptacle to prevent cross-contamination that may skew the results of the sampling. If a ticket is retained, the portable fare device 400 may be configured to print the rider a receipt such that the rider still has proof of a valid transit fare.

In some embodiments, once the tickets are sorted into their respective receptacles, the tickets and/or receptacles may be sent to a lab for application of one or more chemical reagents and/or analysis of the chemical reagents (including any applied at issuance, such as by vending machine 200). In other embodiments, the portable fare device 400 may include an internal printer (not shown) or other device that is configure to apply one or more chemical reagents to the paper tickets based on the matching criteria as the tickets are sorted.

It will be appreciated that in some embodiments the automated ticket devices may only read route data, time data, and/or other non-user specific data for sampling purposes. This ensures that anonymity may be maintained by preventing any data from being read or stored that is associated with a specific user when the ticket is collected. In some embodiments, this may be done using a separate read/scan process (from the scan/read process for transit system access) for sampling purposes. In other embodiments, all data may be read for a particular ticket, but only classification data (no user-specific identification data) is stored.

It will further be appreciated that analysis and sampling may be applied to both single use and multi-use transit tickets. For example, for monthly tickets (or other tickets valid for a particular time period), the tickets may be collected once expired and environmentally sampled. Data from such analysis may be useful in analyzing trends of a contaminant over time in increments matching the time period of validity of the tickets. Additionally, for multi-use tickets having a set number of rides, such as 10-ride passes, the tickets may be collected upon being used for the final ride. For all rides prior to the final ride, the ticket may be returned to the user. In some embodiments, each time the ticket is used it may be collected, with the transit system reissuing a new ticket to the user with one fewer ride on it. In this way, the tickets can be more readily sampled, while still allowing a user to make a single purchase for multiple rides. Single use tickets may be collected after the single use.

Figure 5:
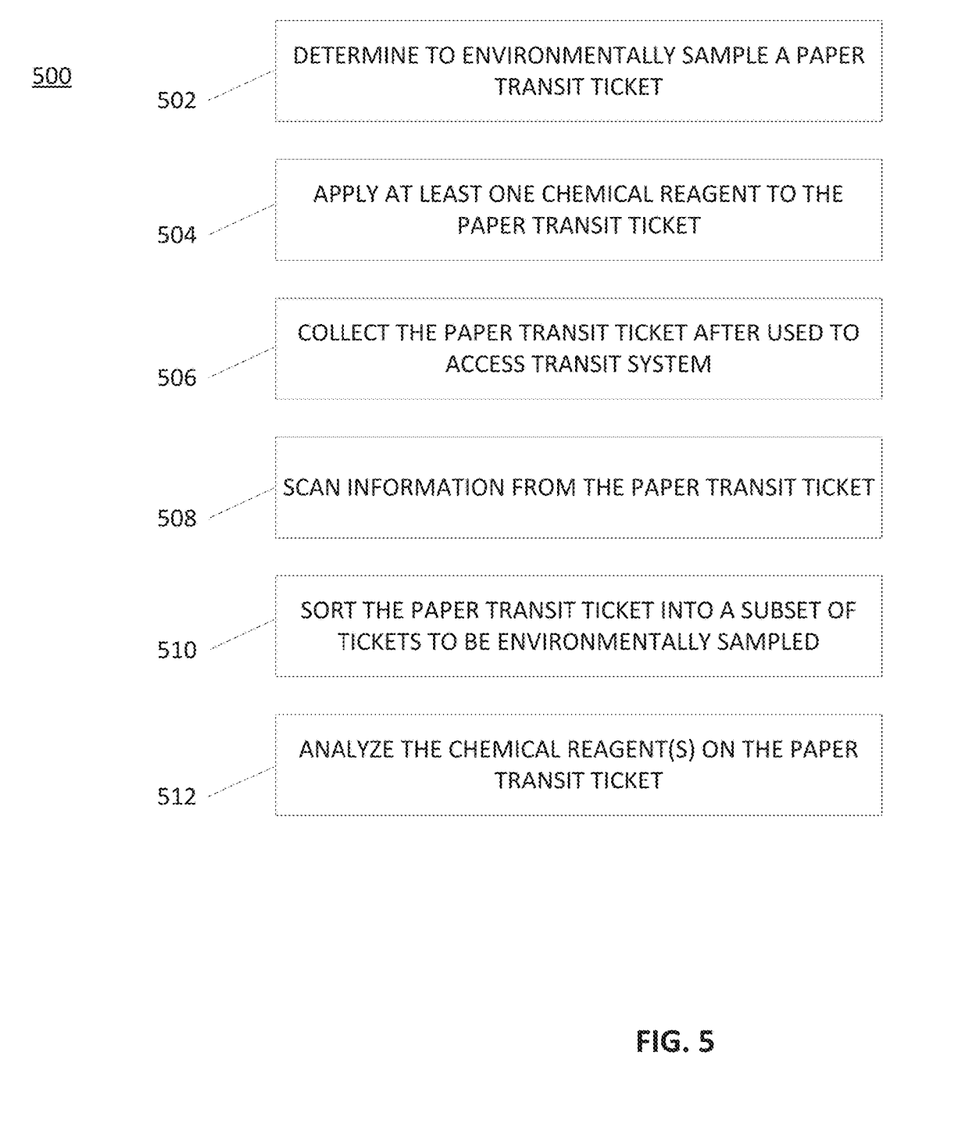
FIG. 5 is a flowchart of a process for environmental sampling according to embodiments.

FIG. 5 depicts a flowchart of a process 500 for environmentally sampling paper transit tickets. Process 500 may be performed using system 100 and the automatic ticket devices described in relation to FIGS. 2-4. Process 500 may begin at block 502 by determining to environmentally sample a particular paper transit ticket for a specific residue. This determination may be made by a transit authority and/or other authority, such as a municipal entity. The determination to sample a particular transit ticket may be based on characteristics of the ticket, such as fare type, time of validity, location of transit for which the ticket is valid, other route characteristics, and/or other factors. These factors and/or other criteria may be communicated to one or more automated ticket devices, such as vending machine 200, ticket collection device 300, and/or portable fare device 400. These automated ticket devices may use such criteria to identify tickets for environmental sampling. For example, a vending machine may compare the criteria to information of a ticket selected by a user for purchase from the vending machine. If the criteria match the selected ticket, the vending machine may determine that the ticket is part of an environmental sampling program, and may take action, such as by applying one or more reagents to the ticket, accordingly. As another example, if a ticket collection device and/or portable fare device scans or otherwise receives a ticket matching the received criteria, the ticket collection device and/or portable fare device may retain the ticket and/or sort the ticket into a subset of like-transit tickets. In some embodiments, the ticket collection device and/or portable fare device may also apply one or more reagents to the ticket based on such a determination.

At block 504, at least one chemical reagent is applied to the particular paper transit ticket. Oftentimes, this may be done using an automated ticket device, such as a ticket vending machine, a transit gate, a fare inspection device, and/or a ticket receptacle. For example, the automated ticket device may include a printer having an ink cartridge filled with at least one chemical reagent. The chemical reagent may then be printed or otherwise applied to paper transit ticket using the printer of the automated ticket device. The chemical reagent may be applied prior to issuance of the ticket, such as by the issuing vending machine or other device. The reagent may also be applied after the ticket has been used to access the transit system, such as by a ticket collection device and/or portable fare device. In some embodiments, one or more reagents may be applied after tickets have been collected for analysis, such as at a remote lab. It will be appreciated that some transit tickets may have reagents applied at multiple locations. As just one example, a single ticket may have one or more reagents applied prior to issuance by the vending machine and after collection, by one or more of a ticket collection device, portable fare device, and/or a lab. Each chemical reagent is selected based on a specific residue that is to be sampled. Oftentimes, the timing of the application of the reagent(s) is based on the particular reagent(s) used. For example, some reagents may not be safe for human contact and/or have short reactive lifespans. These reagents may be applied after collection of the used transit tickets. Reagents that are safe and have longer reactive lifespans may be applied prior to issuance in some embodiments.

At block 506, the particular paper transit ticket is collected after the particular paper transit ticket was used as a fare media within a transit system. This may be done using a ticket collection device, such as a fare gate at an entrance or exit of the transit system, using a portable fare device, and/or using a different automated ticket receptacle. Upon collecting the tickets, transit and/or route data from each ticket may be electronically scanned at block 508, such as by using an optical and/or magnetic scanner of the automated ticket device. The collected paper transit tickets may be automatically sorted into at least one subset paper transit tickets to be environmentally sampled and into at least one subset of the plurality of collected paper transit tickets to not be environmentally sampled at block 510. The sorting may be based at least in part on the transit data on each of the collected paper transit tickets and may be performed automatically using a sorting mechanism coupled with the scanner(s) of the automated ticket device. For example, when the transit information matches the environmental sampling criteria, the tickets may be sorted into subsets of tickets that are to be sampled, with a separate subset for each set of contaminants/reagents. The use of separate subsets for unique combinations of contaminants/reagents to be analyzed helps prevent cross-contamination of contaminants/reagents from tickets that are not within that particular subset.

At block 512, the chemical reagent(s) present on each ticket may be analyzed to determine whether any specific residue or contaminant is present. This analysis may be used to determine a concentration level of the residue on a particular ticket and/or within the subset of tickets. This data, along with the route information for the tickets within the subset, may be used to provide a picture of the presence of a particular contaminant within the transit system and/or municipal area. In some embodiments, results of the analysis may be compared to historical information to determine a trend of the specific residue in a particular location. The analysis may be performed using one of the automated ticket devices and/or at a remote lab. For example, upon the tickets being collected and sorted, the tickets may be sent to the lab for analysis. The results of the analysis may be communicated to a transit authority, municipal authority, such as a police department or environmental organization, and/or other entity.

Figure 6:
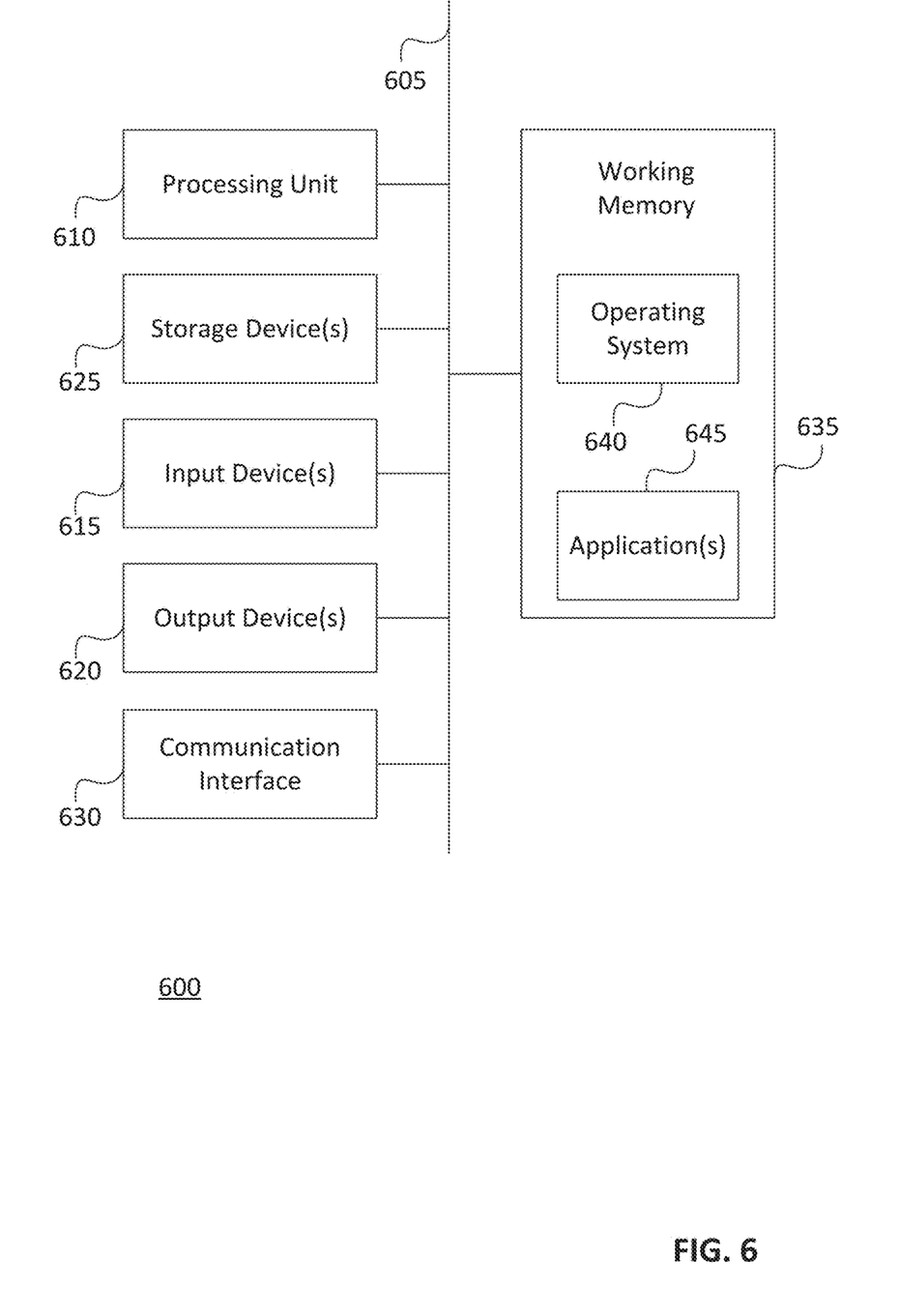
FIG. 6 depicts a computer system according to embodiments.

A computer system as illustrated in FIG. 6 may be incorporated as part of the previously described computerized devices. For example, computer system 600 can represent some of the components of the vending machines, ticket collection devices, portable fare devices, back office computers, lab computers, and the like described herein. FIG. 6 provides a schematic illustration of one embodiment of a computer system 600 that can perform the methods provided by various other embodiments, as described herein. FIG. 6 is meant only to provide a generalized illustration of various components, any or all of which may be utilized as appropriate. FIG. 6, therefore, broadly illustrates how individual system elements may be implemented in a relatively separated or relatively more integrated manner.

The computer system 600 is shown comprising hardware elements that can be electrically coupled via a bus 605 (or may otherwise be in communication, as appropriate). The hardware elements may include a processing unit 610, including without limitation one or more processors, such as one or more special-purpose processors (such as digital signal processing chips, graphics acceleration processors, and/or the like); one or more input devices 615, which can include without limitation a keyboard, a touchscreen, receiver, a motion sensor, a camera, a smartcard reader, a contactless media reader, and/or the like; and one or more output devices 620, which can include without limitation a display device, a speaker, a printer, a writing module, and/or the like.

The computer system 600 may further include (and/or be in communication with) one or more non-transitory storage devices 625, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 600 might also include a communication interface 630, which can include without limitation a modem, a network card (wireless or wired), an infrared communication device, a wireless communication device and/or chipset (such as a Bluetooth™ device, an 502.11 device, a Wi-Fi device, a WiMax device, an NFC device, cellular communication facilities, etc.), and/or similar communication interfaces. The communication interface 630 may permit data to be exchanged with a network (such as the network described below, to name one example), other computer systems, and/or any other devices described herein. In many embodiments, the computer system 600 will further comprise a non-transitory working memory 635, which can include a RAM or ROM device, as described above.

The computer system 600 also can comprise software elements, shown as being currently located within the working memory 635, including an operating system 640, device drivers, executable libraries, and/or other code, such as one or more application programs 645, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such special/specific purpose code and/or instructions can be used to configure and/or adapt a computing device to a special purpose computer that is configured to perform one or more operations in accordance with the described methods.

A set of these instructions and/or code might be stored on a computer-readable storage medium, such as the storage device(s) 625 described above. In some cases, the storage medium might be incorporated within a computer system, such as computer system 600. In other embodiments, the storage medium might be separate from a computer system (e.g., a removable medium, such as a compact disc), and/or provided in an installation package, such that the storage medium can be used to program, configure and/or adapt a special purpose computer with the instructions/code stored thereon. These instructions might take the form of executable code, which is executable by the computer system 600 and/or might take the form of source and/or installable code, which, upon compilation and/or installation on the computer system 600 (e.g., using any of a variety of available compilers, installation programs, compression/decompression utilities, etc.) then takes the form of executable code.

Substantial variations may be made in accordance with specific requirements. For example, customized hardware might also be used, and/or particular elements might be implemented in hardware, software (including portable software, such as applets, etc.), or both. Moreover, hardware and/or software components that provide certain functionality can comprise a dedicated system (having specialized components) or may be part of a more generic system. For example, a risk management engine configured to provide some or all of the features described herein relating to the risk profiling and/or distribution can comprise hardware and/or software that is specialized (e.g., an application-specific integrated circuit (ASIC), a software method, etc.) or generic (e.g., processing unit 610, applications 645, etc.) Further, connection to other computing devices such as network input/output devices may be employed.

Some embodiments may employ a computer system (such as the computer system 600) to perform methods in accordance with the disclosure. For example, some or all of the procedures of the described methods may be performed by the computer system 600 in response to processing unit 610 executing one or more sequences of one or more instructions (which might be incorporated into the operating system 640 and/or other code, such as an application program 645) contained in the working memory 635. Such instructions may be read into the working memory 635 from another computer-readable medium, such as one or more of the storage device(s) 625. Merely by way of example, execution of the sequences of instructions contained in the working memory 635 might cause the processing unit 610 to perform one or more procedures of the methods described herein.

The terms "machine-readable medium" and "computer-readable medium," as used herein, refer to any medium that participates in providing data that causes a machine to operate in a specific fashion. In an embodiment implemented using the computer system 600, various computer-readable media might be involved in providing instructions/code to processing unit 610 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 625. Volatile media include, without limitation, dynamic memory, such as the working memory 635. Transmission media include, without limitation, coaxial cables, copper wire, and fiber optics, including the wires that comprise the bus 605, as well as the various components of the communication interface 630 (and/or the media by which the communication interface 630 provides communication with other devices). Hence, transmission media can also take the form of waves (including without limitation radio, acoustic and/or light waves, such as those generated during radio-wave and infrared data communications).

Common forms of physical and/or tangible computer-readable media include, for example, a magnetic medium, optical medium, or any other physical medium with patterns of holes, a RAM, a PROM, EPROM, a FLASH-EPROM, any other memory chip or cartridge, a carrier wave as described hereinafter, or any other medium from which a computer can read instructions and/or code.

The communication interface 630 (and/or components thereof) generally will receive the signals, and the bus 605 then might carry the signals (and/or the data, instructions, etc. carried by the signals) to the working memory 635, from which the processor(s) 605 retrieves and executes the instructions. The instructions received by the working memory 635 may optionally be stored on a non-transitory storage device 625 either before or after execution by the processing unit 610.

The methods, systems, and devices discussed above are examples. Some embodiments were described as processes depicted as flow diagrams or block diagrams. Although each may describe the operations as a sequential process, many of the operations can be performed in parallel or concurrently. In addition, the order of the operations may be rearranged. Additionally, while the claims may include steps that are identified by a particular letter (a, b, c, etc.) it will be appreciated that these letters are for clarity purposes only and are not to be construed as limiting the order of a claimed process or method as being performed in alphabetical order. As just one example, a method claim having steps ordered a, b, c, d may be performed in any order, such as in the order c, a, b, d. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

What is claimed is:

1. A method for conducting environmental sampling, the method comprising:
    a) determining to environmentally sample a particular paper transit ticket for a specific residue;
    b) applying, using an automated ticket device, at least one chemical reagent to the particular paper transit ticket, the chemical reagent being selected based on the specific residue;
    c) collecting the particular paper transit ticket after the particular paper transit ticket was used as a fare media within a transit system; and
    d) analyzing the at least one chemical reagent to determine whether any of the specific residue is present.

2. The method for conducting environmental sampling of claim 1, wherein:
    the at least one chemical reagent is applied to the particular paper transit ticket prior to issuing the particular paper transit ticket.

3. The method for conducting environmental sampling of claim 1, wherein:
    the at least one chemical reagent is applied to the particular paper transit ticket after collecting the particular paper transit ticket.

4. The method for conducting environmental sampling of claim 1, wherein:
    the determination to environmentally sample the particular printed transit ticket for the specific residue is based at least in part on the particular paper transit ticket having route characteristics matching a set of predetermined environmental sampling criteria.

5. The method for conducting environmental sampling of claim 1, wherein:
    a) the at least one chemical reagent comprises a first chemical reagent and a second chemical reagent;
    b) the first chemical reagent is applied to the particular paper transit ticket prior to issuing the particular paper transit ticket; and
    c) the second chemical reagent is applied to the particular paper transit ticket after collecting the particular paper transit ticket.

6. The method for conducting environmental sampling of claim 1, wherein:
a timing of the application of the at least one chemical reagent is based on at least one characteristic of the at least one chemical reagent being applied.

7. The method for conducting environmental sampling of claim 1, wherein:
the automated ticket device comprises a ticket receptacle.

8. The method for conducting environmental sampling of claim 1, further comprising:
comparing results of the analysis of the at least one chemical reagent to historical information to determine a trend of the specific residue in a particular location.

9. The method for conducting environmental sampling of claim 1, further comprising:
providing a printer in the automated device; and
supplying the printer with an ink cartridge filled with the at least one chemical reagent, wherein applying the at least one chemical reagent comprises printing the at least one chemical reagent onto the particular paper transit ticket using the printer at the automated device.

10. The method for conducting environmental sampling of claim 1, wherein:
analyzing the at least one chemical reagent comprises determining a concentration level of the specific residue.

11. The method for conducting environmental sampling of claim 1, further comprising:
electronically scanning transit data on a plurality of collected paper transit tickets; and
sorting the plurality of collected paper transit tickets into at least one subset of the plurality of collected paper transit tickets to be environmentally sampled and into at least one subset of the plurality of collected paper transit tickets to not be environmentally sampled, wherein the sorting is based at least in part on the transit data on each of the plurality of collected paper transit tickets.

* * * * *